United States Patent
Dörr et al.

(10) Patent No.: US 9,228,049 B2
(45) Date of Patent: Jan. 5, 2016

(54) METHOD FOR PRODUCING HYDROPHILIC, ALIPHATIC POLYURETHANE FOAMS HAVING LOW BULK DENSITY

(75) Inventors: Sebastian Dörr, Düsseldorf (DE); Meike Niesten, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 192 days.

(21) Appl. No.: 13/805,698

(22) PCT Filed: Jun. 20, 2011

(86) PCT No.: PCT/EP2011/060217
§ 371 (c)(1),
(2), (4) Date: Jan. 11, 2013

(87) PCT Pub. No.: WO2011/161048
PCT Pub. Date: Dec. 29, 2011

(65) Prior Publication Data
US 2013/0109774 A1 May 2, 2013

(30) Foreign Application Priority Data
Jun. 22, 2010 (EP) .................................... 10166831

(51) Int. Cl.
*C08G 18/83* (2006.01)
*A61L 15/26* (2006.01)
*A61L 15/42* (2006.01)
*C08G 18/10* (2006.01)
*C08G 18/08* (2006.01)
*C08G 18/48* (2006.01)

(52) U.S. Cl.
CPC ............... *C08G 18/833* (2013.01); *A61L 15/26* (2013.01); *A61L 15/425* (2013.01); *C08G 18/10* (2013.01); *C08G 18/14* (2013.01); *C08G 18/4833* (2013.01); *C08G 18/4837* (2013.01)

(58) Field of Classification Search
CPC ...................................................... C08G 18/14
USPC ............................................................ 521/159
See application file for complete search history.

(56) References Cited

U.S. PATENT DOCUMENTS

2009/0118387 A1* 5/2009 Sakakibara .................... 521/170
2011/0184080 A1 7/2011 Schonberger et al.

FOREIGN PATENT DOCUMENTS

EP 2143744 A1 1/2010

OTHER PUBLICATIONS

International Search Report for PCT/EP2011/060217 mailed Oct. 17, 2011.

* cited by examiner

*Primary Examiner* — Melissa Rioja
(74) *Attorney, Agent, or Firm* — Drinker Biddle & Reath LLP

(57) ABSTRACT

The invention relates to a method for producing hydrophilic, aliphatic polyurethane foams having low bulk density. The invention further relates to hydrophilic, aliphatic polyurethane foams that can be obtained according to the method, and to the use thereof as a wound dressing, incontinence product, or as a cosmetic article.

20 Claims, No Drawings

METHOD FOR PRODUCING HYDROPHILIC, ALIPHATIC POLYURETHANE FOAMS HAVING LOW BULK DENSITY

RELATED APPLICATIONS

This application is a national stage application (under 35 U.S.C. §371) of PCT/EP2011/060217, filed Jun. 20, 2011, which claims benefit of European application 10166831.7, filed Jun. 22, 2010.

The invention relates to a method for producing hydrophilic aliphatic polyurethane foams having low bulk density. The invention also relates to a hydrophilic aliphatic polyurethane foam obtainable according to said method and to the use of said foam as wound dressing, incontinence product or cosmetic article.

European patent application EP 2 143 744 discloses a method which can be used to produce hydrophilic aliphatic polyurethane foams. The method comprises reacting isocyanate-functional prepolymers with $C_8$- to $C_{22}$-monocarboxylic acids or their ammonium or alkali metal salts or $C_{12}$- to $C_{44}$-dicarboxylic acids or their ammonium or alkali metal salts and water. The prepolymers are obtainable by reacting low molecular weight aliphatic diisocyanates with di- to hexafunctional polyalkylene oxides. The components are mixed and introduced into a beaker in which the foaming reaction then takes place. A slabstock polyurethane foam is obtained. It is cut to the desired thickness of typically 10μ to 5 cm when it is to be used as wound dressing for example.

The process of EP 2 143 744 A1 uses exclusively prepolymers containing less than 1 percent by weight low molecular weight aliphatic diisocyanates. In this way the intention is to ensure that the complete foam no longer contains any extractable free low molecular weight aliphatic diisocyanates, the release of which from wound dressings is considered to be objectionable from a health standpoint.

It was desirable to possess a process which could be used to produce foams having a lower bulk density than the foams obtainable by the known process. A low bulk density is advantageous since less material is needed for a given volume and since rapid and effective transport of moisture is possible as a result of the high pore fraction and the associated capillary action.

The problem addressed by the present invention was therefore that of specifying a simple method for producing hydrophilic aliphatic polyurethane foams having low bulk density and a low proportion of extractable free isocyanates.

This problem is solved by the method of claim 1, which comprises

I) preparing isocyanate-functional prepolymers A) by reaction of
low molecular weight aliphatic diisocyanates A1) having a molar mass of 140 to 278 g/mol with
di- to hexafunctional polyalkylene oxides A2) having an OH number of 22.5 to 112 mg KOH/g and an ethylene oxide fraction of 50 to 100 mol %, based on the total amount of oxyalkylene groups present,
using a molar excess of low molecular weight aliphatic diisocyanates A1), II) at least partly removing the unreacted excess of low molecular weight aliphatic diisocyanates A1), III) preparing a mixture of low molecular weight aliphatic diisocyanates A1) with the prepolymers A), the free low molecular weight aliphatic diisocyanate content of said mixture being 1 to 15 wt. %, IV) mixing the mixture of step III) with C8- to C22-monocarboxylic acids or their ammonium or alkali metal salts or C12- to C44-dicarboxylic acids or their ammonium or alkali metal salts B) and water C), and V) foaming and curing the mixture of step IV).

Surprisingly it has been found that by means of the method of the present invention it is possible to obtain polyurethane foams which not only have lower bulk density in comparison to foams produced by the known process but also, furthermore, do not have a higher fraction of extractable free isocyanates.

In accordance with one preferred embodiment of the invention it is possible in step III) to prepare a mixture having a low molecular weight aliphatic diisocyanate A1) content of 1.5 to 10 and preferably of 2.0 to 8 wt. %. In that case, foams with a particularly low bulk density are obtained.

It is also preferred if in step II) the excess of diisocyanate A1) is removed by thin film distillation, since this technique allows easy and comprehensive removal.

Foams with a particularly low density are also obtained when the NCO content of the mixture III), determined in accordance with DIN-EN ISO11909, is 4 to 10 wt. %.

The low molecular weight aliphatic diisocyanates A1) used in steps I) and III) have in each case a molar mass of 140 to 278 g/mol. They are preferably in each case monomolecular compounds. With particular preference, the low molecular weight aliphatic diisocyanates A1) in step I) and the low molecular weight aliphatic diisocyanates A1) in step III) are identical compounds.

Examples of low molecular weight aliphatic diisocyanates of component A1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, of which hexamethylene diisocyanate, isophorone diisocyanate, butylene diisocyanate and bis(isocyanatocyclohexyl)methane are preferable. Hexamethylene diisocyanate, isophorone diisocyanate and butylene diisocyanate are more preferable and hexamethylene diisocyanate and isophorone diisocyanate are most preferable.

It is also preferable when the diisocyanate A1) used is exclusively hexamethylene diisocyanate and isophorone diisocyanate or mixtures thereof.

The polyalkylene oxides A2) are preferably copolymers of ethylene oxide and propylene oxide which were started on polyols or amines and have an ethylene oxide content, based on the total amount of oxyalkylene groups present, of 50 to 100 mol % and preferably of 60 to 85 mol %. Suitable starter molecules of this kind are glycerol, trimethylolpropane (TMP), sorbitol, pentaerythritol, triethanolamine, ammonia or ethylenediamine.

The polyalkylene oxides A2) typically have number-average molecular weights of 1000 to 15 000 g/mol and preferably of 3000 to 8500 g/mol.

The polyalkylene oxides A2) may further have OH functionalities of 2 to 6, preferably of 3 to 6 and more preferably of 3 to 4.

In a further development of the invention, the polyalkylene oxides A2) used are copolymers of ethylene oxide and propylene oxide having an ethylene oxide content, based on the total amount of oxyalkylene groups present, of 60 to 85 mol % and started on polyols or amines.

The reaction of the diisocyanates A1) with the polyalkylene oxides A2) can be carried out in the presence of urethanization catalysts such as tin compounds, zinc compounds, amines, guanidines or amidines, or in the presence of allophanatization catalysts such as zinc compounds.

The reaction temperature can typically be in the range from 25 to 140° C. and preferably in the range from 60 to 100° C.

Component B) can utilize ammonium and alkali metal salts of $C_8$- to $C_{22}$-monocarboxylates or their free carboxylic acids or ammonium and alkali metal salts of $C_{12}$- to $C_{44}$-dicarboxylates or their free dicarboxylic acids, preferably potassium or sodium salts of $C_8$- to $C_{22}$-monocarboxylates or $C_{12}$- to $C_{44}$-dicarboxylates and more preferably sodium salts of $C_8$- to $C_{22}$-monocarboxylates.

Examples of suitable compounds of component B) are the ammonium, sodium, lithium or potassium salts of ethylhexanoic acid, octanoic acid, decanoic acid, dodecanoic acid, palmitic acid, stearic acid, the octadecenoic acids, the octadecadienoic acids, the octadecatrienoic acids, isostearic acid, erucic acid, abietic acid and hydrogenation products thereof. Examples of $C_{12}$- to $C_{44}$-dicarboxylic acids and the ammonium and alkali metal salts derived therefrom are dodecanedioic acid, dodecenylsuccinic acid, tetradecenylsuccinic acid, hexadecenylsuccinic acid, octadecenylsuccinic acid, $C_{36}$ and $C_{44}$ dimer fatty acids and hydrogenation products thereof and also the corresponding ammonium, sodium, lithium or potassium salts of these dicarboxylic acids.

The water to be used as component C) can be used as such, as water of crystallization of a salt, as solution in a dipolar aprotic solvent or else as an emulsion. Preferably, the water is used as such or in a dipolar aprotic solvent.

In a further possible embodiment, the mixture of step IV) optionally contains catalysts D), surfactants E), alcohols F) and/or blowing agents G).

Catalysts D) can be especially metal salts, amines, amidines and guanidines used alone or in combination.

Compounds of component E) can be used to improve foam formation, foam stability or the properties of the resulting polyurethane foam, in which case such additives can in principle be any anionic, cationic, amphoteric and nonionic surfactants known per se and also mixtures thereof. Preference is given to using alkylpolyglycosides, EO-PO block copolymers, alkyl or aryl alkoxylates, siloxane alkoxylates, esters of sulfosuccinic acid and/or. Particular preference is given to using EO-PO block copolymers. Preferably, the EO-PO block copolymers are solely used as component F).

In addition, compounds of component F) can be used to improve the foam properties of the resulting polyurethane foam. These compounds comprise in principle any mono- and polyhydric alcohols known per se to a person skilled in the art, and also mixtures thereof. These are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyether diols and polyester diols.

Foaming can in principle be effected by means of the carbon dioxide formed in the course of the reaction of the isocyanate groups with water, but the use of further blowing agents G) is likewise possible. It is thus also possible in principle to use blowing agents from the class of the hydrocarbons such as $C_3$-$C_6$ alkanes, for example butanes, n-pentane, isopentane, cyclopentane, hexanes or the like, or halogenated hydrocarbons such as dichloromethane, dichloromonofluoromethane, chlorodifluoroethanes, 1,1-dichloro-2,2,2-trifluoroethane, 2,2-dichloro-2-fluoro-ethane, particularly chlorine-free hydrofluorocarbons such as difluoromethane, trifluoromethane, difluoroethane, 1,1,1,2-tetrafluoroethane, tetrafluoroethane (R 134 or R 134a), 1,1,1,3,3-pentafluoropropane (R 245 fa), 1,1,1,3,3,3-hexafluoropropane (R 256), 1,1,1,3,3-pentafluorobutane (R 365 mfc), heptafluoropropane, or else sulfur hexafluoride. Mixtures of these blowing agents can also be used.

In a preferred embodiment of the invention, the components A) to F) are used in the following amounts:
- 100 parts by weight of the mixture of step III),
- 0.1 to 5 parts by weight of C8- to C22-monocarboxylic acids or their ammonium or alkali metal salts or C12- to C44-dicarboxylic acids or their ammonium or alkali metal salts B),
- 1 to 200 parts by weight of water C),
- 0 to 1 part by weight of catalysts D),
- 0 to 10 parts by weight of surfactants E),
- 0 to 20 parts by weight of alcohols F).

Particular preference is given to using components A) to F) in the following amounts:
- 100 parts by weight of the mixture of step I),
- 0.1 to 5 parts by weight of C8- to C22-monocarboxylic acids or their ammonium or alkali metal salts or C12- to C44-dicarboxylic acids or their ammonium or alkali metal salts B),
- 2 to 100 parts by weight of water C),
- 0 to 1 part by weight of catalysts D),
- 0 to 10 parts by weight of surfactants E),
- 0 to 20 parts by weight of alcohols F).

Very particular preference is given to using components A) to F) in the following amounts:
- 100 parts by weight of the mixture of step I),
- 0.1 to 5 parts by weight of C8- to C22-monocarboxylic acids or their ammonium or alkali metal salts or C12- to C44-dicarboxylic acids or their ammonium or alkali metal salts B),
- 3 to 50 parts by weight of water C),
- 0 to 1 part by weight of catalysts D),
- 0 to 10 parts by weight of surfactants E),
- 0 to 20 parts by weight of alcohols F).

Temperatures for commixing the components and/or mixtures and during the foaming reaction can be in the range from 0 to 100° C., preferably at from 15 to 70° C. and most preferably at from 20 to 50° C.

After mixing the component, the mixture can be applied to a sheetlike substrate as a layer of constant thickness. Examples of suitable substrates are release foils or release papers, which may be in an apertured state.

It may be preferable to apply the mixture to the substrate by blade coating. For this, the mixture may be poured into a blade-coating box and be blade-coated horizontally in a certain thickness in sheetlike mats onto a suitable substrate such as, for example, a release foil or a release paper.

Blade gap height here is generally in the range from 0.2 to 20 mm, preferably in the range from 0.2 to 5 mm and most preferably in the range from 0.2 to 2 mm. The film width of the blade to be used can be conformed to the particular intended purpose. Examples are film widths between 10 and 5000 mm and preferably between 10 and 4000 mm.

Any known type of blade coater can be used, for example a floating knife coater, a knife-on-roll coater, a spreading-blade coater, a box-type blade coater, a blade-knife coater or a magnetic squeegee coater. Any customary material can be used for the blade, for example metals such as stainless steel or plastics. A composite of two or more materials can also be used to produce the blade. Both manual coaters and machine coaters can be used, preference being given to the use of machine coaters as part of suitable coating rigs. Application between rolls is another possibility.

Directly after application, an apertured release element can be placed sheetlike on the layer of the mixture, so that it covers the substrate-remote surface of the layer.

Apertured herein is understood as referring to a release element which has a multiplicity of apertures extending from the contact face through the release element.

The apertures preferably have a circular diameter.

It is also preferable for the apertures to form a uniform distribution across the release element.

The apertures may preferably have a diameter of 20 to 300 µm. This provides foams with no visible elevations on the surface of the foam in the shape of the release element apertures. The foams have a smooth surface, as is particularly advantageous for their use as wound dressing, since wound dressings shall ideally conform to the body sheetlike.

The separation between two adjacent apertures is preferably between 0.1 to 5 mm, more preferably between 0.5 to 3 mm and most preferably between 0.8 and 2.5 mm.

The apertured release element may be for example an apertured release paper or an apertured release foil. The release paper may be, for example, siliconized paper, polyolefin-coated paper or fluorocarbon-coated paper. Similarly, the release foil may consist of silicone, polyolefins and/or fluorocarbon and/or be coated with materials of this type.

After the release element has been applied, it may more particularly be preferable to apply a defined downward pressure on the layer composed of the mixture of step IV).

To speed the curing of the polyurethane foam on completion of its expansion, it can be heated. It may be preferable to heat the polyurethane foam to a temperature of 40 and 140° C., more preferably of 60 to 120° C. and even more preferably of 60 to 110° C.

Particular preference is also given to a process wherein a wound dressing is produced from the polyurethane foam of the present invention.

Further subjects of the invention are a polyurethane foam obtainable according to the method of the present invention.

The polyurethane foams obtained have a porous, at least partially open-cell structure having intercommunicating cells.

The polyurethane foams may be adhered to or laminated or coated with further materials, for example materials based on hydrogels, (semi)permeable films, foam films, coatings, hydrocolloids or other foams.

The polyurethane foams of the present invention are particularly useful in the manufacture of wound dressings. In these dressings, the polyurethane foams can be in direct or indirect contact with the wound. Preferably, however, the polyurethane foams are used in direct contact with the wound in order that optimum absorbance of wound fluid may be ensured for example. The polyurethane foams exhibit no cytotoxicity (determined according to ISO 10993-5 and ISO 10993-12).

The polyurethane foams which are used as wound dressing can be additionally sterilized in a further operation. The sterilization is effected using processes known per se to a person skilled in the art, wherein sterilization is effected by thermal treatment, chemical substances such as ethylene oxide or irradiation, for example by gamma irradiation. Irradiation here may be carried out under protective gas atmosphere, where appropriate. The polyurethane foams of the present invention here have the immense advantage of not discoloring on irradiation, in particular on irradiation with gamma rays.

It is likewise possible to add, incorporate or coat antimicrobially or biologically active components which have a positive effect for example in relation to wound healing and the avoidance of germ loads.

The invention finally also provides a hydrophilic aliphatic polyurethane foam of the present invention for use as wound dressing, incontinence product or cosmetic article.

EXAMPLES

Unless stated otherwise, all percentages are by weight. Solids contents were determined according to DIN-EN ISO 3251. Viscosities were determined at 23° C. to DIN 53019. NCO contents were determined volumetrically in accordance with DIN-EN ISO 11909.

Determination of Extract Volume:

48 hours: 10 g of the foam were placed in 300 ml of fully demineralized water at 37° C. for 48 hours and the extract volume was determined by titrating the chemical oxygen demand in accordance with DIN EN 1484.

7 days: 4.7 g of the foam were placed in 220 ml of fully demineralized water at 37° C. for 7 days and the extract volume was determined by titrating the chemical oxygen demand in accordance with DIN EN 1484.

Determination of Bulk Density:

Bulk density was determined by first weighing a piece of the respective foam measuring 10×10×5 cm. The bulk density was subsequently calculated by dividing the mass of the foam by its volume.

Substances and Abbreviations Used:

Carboxylate 1: 5% sodium oleate in water

Desmodur® N 3400: aliphatic polyisocyanate (HDI uretdione), NCO content 21.8%

DBU 1,8-diazabicyclo[5.4.0]undecene-7

Example 1

Preparing Polyurethane Prepolymer 1, Thin Film Method, Component for the Defined Admixture with Monomeric Diisocyanate To a mixture of 1000 g of hexamethylene diisocyanate (HDI) and 1 g of benzoyl chloride, 1000 g of a glycerol-started polyalkylene oxide having a molar mass of 4680 g/mol, an ethylene oxide weight fraction of 72% and a propylene oxide weight fraction of 28%, which had been dried beforehand at 100° C. for 2 h at a pressure of 10 mbar, were added by dropwise addition at 80° C. in the course of 3 h and subsequently stirred for 12 h. Excess HDI was removed by thin film distillation at 130° C. and 0.1 mbar, while the non-volatile constituents were stabilized with 1 g of chloropropionic acid to obtain a prepolymer having an NCO content of 2.8% and a viscosity of 3500 mPas.

Examples 2 and 3, Comparative Examples 1 and 2

Production of Foams

The isocyanate components were homogenized at a stirrer speed of 1200 rpm for 15 seconds. The further components were then weighed in, and the components were stirred together for a further 10 seconds. The mixture, lastly, was poured into a paper mold measuring 15×15×15 (width× height×length). The oligomer employed, if one was used, was in each case Desmodur® N 3400; as carboxylate, a 5% strength by weight solution of sodium oleate in water was used. In addition, added water is indicated as an extra.

|  | 2 | 3 | Comparative Example 1 | Comparative Example 2 |
|---|---|---|---|---|
| Prepolymer DSB 3227 | 75 | 75 | 75 | 75 |
| HDI | 5.3 | 8.1 | | |
| Oligomer (N3400) | 0 | 0 | | 8.33 |
| NCO content of mixture (%) | 4.6 | 6 | 2.6 | 4.6 |
| Water | 3.35 | 3.35 | 3.35 | 3.35 |
| DBU | 0.05 | 0.05 | 0.05 | 0.05 |
| Sodium oleate (building block E) as 5% strength by weight solution in water | 8.15 | 8.15 | 8.15 | 8.15 |
| Bulk density [g/1000 cm$^3$] | 71 | 83 | 199 | 109 |
| Extract EN 1484 wt. % | | | | |
| 48 h | 0.11 | 0.08 | not determined | 0.11 |
| 7 d | 0.13 | 0.11 |  | 0.15 |

Examples 2 and 3 show that foams with a bulk density of less than 100 g/l can be produced on the basis of prepolymers comprising free low molecular weight aliphatic diisocyanate. The extract volume in these foams is not greater than that of the foam from Comparative Example 2, which is based on a thin-film-treated prepolymer which is free from monomeric diisocyanate.

Comparative Example 1 shows that foams produced from thin-film-treated prepolymer without a free diisocyanate being added additionally have a significantly higher density.

The invention claimed is:

1. A method for producing hydrophilic aliphatic polyurethane foam which comprises
   I) preparing an isocyanate-functional prepolymer A) by reacting
      a low molecular weight aliphatic diisocyanate A1) having a molar mass of 140 to 278 g/mol with
      a di- to hexafunctional polyalkylene oxide A2) having an OH number of 22.5 to 112 mg KOH/g and an ethylene oxide fraction of 50 to 100 mol %, based on the total amount of oxyalkylene groups present,
   using a molar excess of low molecular weight aliphatic diisocyanate A1),
   II) at least partly removing the unreacted excess of low molecular weight aliphatic diisocyanate A1),
   III) obtaining a mixture of step III of low molecular weight aliphatic diisocyanate A1) with the isocyanate-functional prepolymer A), the free low molecular weight aliphatic diisocyanate content of said mixture of step III being 2.0 to 15 weight %,
   IV) preparing a mixture of step IV by mixing the mixture of step III) with C8- to C22-monocarboxylic acid or their ammonium or alkali metal salt or C12- to C44-dicarboxylic acid or their ammonium or alkali metal salt B) and water C), and
   V) foaming and curing the mixture of step IV) to prepare a polyurethane foam.

2. The method of claim 1, wherein the mixture of step III) has a low molecular weight aliphatic diisocyanate A1) content of 2.0 to 10 weight %.

3. The method of claim 1, wherein the mixture of step III) has a low molecular weight aliphatic diisocyanate A1) content of 2.0 to 8 weight %.

4. The method of claim 1, wherein in step II) the excess of the aliphatic diisocyanate A1) is removed by thin film distillation.

5. The method of claim 1, wherein the NCO content of the mixture of step III), determined to DIN-EN ISO 11909, is 4 to 10 weight %.

6. The method of claim 1, wherein the low molecular weight aliphatic diisocyanate A1) is hexamethylene diisocyanate, isophorone diisocyanate or a mixture thereof.

7. The method of claim 1, wherein the di- to hexafunctional polyalkylene oxide A2) is a copolymer of ethylene oxide and propylene oxide having an ethylene oxide content, based on the total amount of oxyalkylene groups present, of 60 to 85 mol %.

8. The method of claim 1, wherein the di- to hexafunctional polyalkylene oxide A2) has a number-average molecular weight of 3000 to 8500 g/mol.

9. The method of claim 1, wherein the di- to hexafunctional polyalkylene oxide A2) has OH functionalities of 3 to 4.

10. The method of claim 1, wherein the mixture of step IV) contains a catalyst D), a surfactant E), an alcohol F) and/or a blowing agent G) other than water.

11. The method of claim 10, wherein catalyst D) is metal salt, amine, amidine or guanidine or a mixture thereof.

12. The method of claim 10, using the following
   100 parts by weight of the mixture of step III),
   0.1 to 5 parts by weight of C8- to C22-monocarboxylic acid or their ammonium or alkali metal salt or C12- to C44-dicarboxylic acid or their ammonium or alkali metal salt B),
   1 to 200 parts by weight of water C),
   0 to 1 part by weight of catalyst D),
   0 to 10 parts by weight of surfactant E), and
   0 to 20 parts by weight of alcohol F).

13. The method of claim 1, wherein the polyurethane foam on completion of foaming is heated to speed curing.

14. The method of claim 13, wherein the polyurethane foam on completion of foaming is heated to a temperature of 40 to 140° C.

15. The method of claim 13, wherein the polyurethane foam on completion of foaming is heated to a temperature of 60 to 110° C.

16. The method of claim 1, wherein a wound dressing is produced from the polyurethane foam.

17. A hydrophilic aliphatic polyurethane foam obtained by the method of claim 1.

18. The hydrophilic aliphatic polyurethane foam of claim 17, wherein the foam is a wound dressing, an incontinence product or a cosmetic article.

19. A method of preparing a composition for treating wounds which comprises utilizing the hydrophilic aliphatic polyurethane foam of claim 17.

20. A wound dressing, an incontinence product or a cosmetic article which comprises the hydrophilic aliphatic polyurethane foam of claim 17.

* * * * *